United States Patent [19]
Sands et al.

[11] Patent Number: 5,948,952
[45] Date of Patent: Sep. 7, 1999

[54] XERODERMA PIGMENTOSUM-DEFICIENT MOUSE

[75] Inventors: Arthur T. Sands, The Woodlands; Alejandro Abuin; Allan Bradley, both of Houston, all of Tex.

[73] Assignee: Baylor College of Medicine, Houston, Tex.

[21] Appl. No.: 08/708,958

[22] Filed: Sep. 6, 1996

[51] Int. Cl.$^6$ .............................. C12N 5/00; C12N 5/06; G01N 33/567; A61K 49/00

[52] U.S. Cl. ...................... 800/3; 800/9; 800/18; 424/9.1; 424/9.2; 435/325.1; 435/354; 435/7.21; 435/455; 435/29

[58] Field of Search .............................. 800/2, DIG. 1–4; 424/9.1, 9.2; 435/172.3, 240.1, 240.2, 4, 29, 40.51, 40.52, 325, 325.1, 354

[56] References Cited

PUBLICATIONS

Sands et al, *Nature*, 377:162–165 (1995).
Cheo et al, *J. Cell. Biochem., Abstract Supplement 21A*:309, Abstract No. C5–328, 24th Annual Keystone (1995).
Li et al, *Nature Genetics*, 5:413–147 (1993).
Legerski et al, *Nature*, 359:70–73 (1992).
Cleaver, *Cell*, 76:1–4 (1994).
Cleaver et al, *The Metabolic Basis of Inherited Disease*, pp. 4393–4419 (McGraw–Hill, New York (1995)).
Cheo et al. Characterization of defective nucleotide excision repair in XPC mutant mice. Mutation Research, vol. 374, pp. 1–9, 1997.
Fassler et al. Knockout Mice: How to Make them and Why. Int. Arch. Allergy Immunol., vol. 106, pp. 323–334, 1995.

*Primary Examiner*—Deborah Crouch
*Assistant Examiner*—Deborah J. R. Clark
*Attorney, Agent, or Firm*—Pennie & Edmonds LLP

[57] ABSTRACT

An Xeroderma pigmentosum-deficient mouse, as well as methods for screening for the damaging and tumorigenic effect of ultraviolet light or a chemical DNA damaging agent, are disclosed.

14 Claims, 5 Drawing Sheets

FIG. 2

```
mXPC    QGRPHARKRRVAAKVSYKEESESDGAGSGSDFEPSSGEGQHSSDEDCEPG
        | |||:|.||||.:|||||||:||:||||||||  ||||: ..|||:|||
hXPC    QRRPHGRERRVASRVSYKEESGSDEAGSGSDFELSSGEASDPSDEDSEPG mXPC    PCKQKRASAPQRTKAGSKSASKTQRGSQCEPSSFPEASSSSSGCKRGKKV
        |.||::|.|||||||||||||:|:|||: ...|:|.||||||::||||:
hXPC    PPKQRKAPAPQRTKAGSKSASRTHRGSHRKDPSLPAASSSSSSSKRGKKM mXPC    SSGAEEMADRKPAGVDQWLEVYCEPQAKWVCVDCVHGVVGQPVACYKYAT
        |::|. ..|. ||:||||||:||.::.||||||||||||||:.||||||
hXPC    CSDGEKAEKRSIAGIDQWLEVFCEQEEKWVCVDCVHGVVGQPLTCYKYAT mXPC    KPMTYVVGIDSDGWVRDVTQRYDPAWMTATRKCRVDAEWWAETLRPYRSL
        ||||||||||||||||||||||||||.|||.||||||||||||||||.|
hXPC    KPMTYVVGIDSDGWVRDVTQRYDPVWMTVTRKCRVDAEWWAETLRPYQSP mXPC    LTEREKKEDQE
        : :||||||| |
hXPC    FMDREKKEDLE
```

XERODERMA PIGMENTOSUM-DEFICIENT MOUSE

This development of the present invention was supported, in part, by NIH Grant Nos. R01 DK46001 and R01 AD24613. The Government has certain rights to this invention.

FIELD OF THE INVENTION

The present invention relates to, inter alia, an Xeroderma pigmentosum-deficient mouse, as well as methods for screening for the damaging and tumorigenic effect of ultraviolet light or a chemical DNA damaging agent.

BACKGROUND OF THE INVENTION

DNA repair is required by organisms to prevent the accumulation of mutations and to maintain the integrity of genetic information. Compromise of genetic information may result in dysregulation of cellular growth control, and ultimately tumor formation. Nucleotide excision repair (NER) removes a broad spectrum of DNA mutations, including ultraviolet light-induced photo-products, bulky chemical adducts, intrastrand cross-links, and interstrand cross-links (Weeda et al, *BioEssays,* 15:249 (1993)).

Xeroderma pigmentosum (XP) is a rare autosomal recessive disease. Cells cultured from XP patients have an increased sensitivity to ultraviolet light (UV), and a phenotype related to defective NER (Cleaver, *Nature,* 218:652 (1968)). This disease is characterized primarily by hypersensitivity of the skin to sunlight, with cutaneous symptoms that may include pigmentation abnormalities, and a greater than 1000-fold increased risk of skin cancers in sun-exposed parts of the body (Cleaver, In: *The Metabolic Basis of Inherited Disease,* McGraw Hill, New York (1995)). XP is a heterogenous disease, with some patients exhibiting progressive neurologic degeneration, as well as sensitivity to sunlight. Cell fusion complementation studies have revealed eight complementation groups in XP (A-G, and an XP-variant form) (Cleaver, supra).

XP group C (XPC) is one of the most common forms of the disease, and is characterized by an NER defect in transcription-independent repair, with apparently normal rates of repair of the transcribed strand of active genes (Venema et al, *Mol. Cell. Biol.,* 11:4128 (1991)). In rodents afflicted with XPC, the large untranscribed regions of the genome remain unrepaired, while small actively transcribed regions are repaired (Bohr, *Carcinogenesis,* 12:1983 (1991)).

The human xpc gene has been cloned by complementation of the NER defect, and found to contain a region of homology to the yeast RAD4 gene (Legerski et al, *Nature,* 359:70 (1992)). The human xpc gene has been found to be mutated in cell lines from XPC patients (Li et al, *Nature Genetics,* 5:413 (1993)). Thus, the cloning of the human xpc gene has allowed for genetic screening of XPC in humans. However, heretofore, there has been no animal model for XPC to allow for screening for the damaging and tumorigenic effect of ultraviolet light and chemical DNA damaging agents. The present invention has provided for the first time such an animal model for XPC.

SUMMARY OF THE INVENTION

An object of the present invention is to provide an animal model for XPC.

An additional object of the present invention is to provide mouse cells which are XPC-deficient.

Another object of the present invention is to provide a mouse which is XPC-deficient.

Still another object of the present invention is provide a method for screening for the damaging and tumorigenic effect of ultraviolet light and chemical DNA damaging agents using mouse cells which are XPC-deficient.

Yet another object of the present invention is provide a method for screening for the damaging and tumorigenic effect of ultraviolet light and chemical DNA damaging agents using a mouse which is XPC-deficient.

These and other objects of the present invention, which will be apparent from the detailed description of the invention provided hereinafter, have been met, in one embodiment, by a mouse cell comprising two chromosomal alleles of the xpc gene, wherein at least one of said alleles contains a mutation such that said cell produces less than wild-type levels of XPC activity.

In another embodiment of the present invention, the above-described objects have been met by a mutant mouse which produces less than wild-type levels of XPC activity as a result of a mutation in the xpc gene.

In still another embodiment of the present invention, the above-described objects have been met by a method for screening for the damaging and tumorigenic effect of ultraviolet light or a chemical DNA damaging agent comprising the steps of:

(1) exposing mouse cells, which produce less than wild-type levels of XPC activity as a result of a mutation in the xpc gene, to UV light or a chemical DNA damaging agent; and (2) evaluating cytotoxicity in the resulting exposed cells.

In still another embodiment of the present invention, the above-described objects have been met by a method for screening for the damaging and tumorigenic effect of ultraviolet light or a chemical DNA damaging agent comprising the steps of:

(1) exposing skin of a mutant mouse, which produces less than wild-type levels of XPC activity as a result of a mutation in the xpc gene, to UV light or a chemical DNA damaging agent; and (2) evaluating pathology in the resulting exposed mouse.

BRIEF DESCRIPTION OF THE DRAWINGS

FIG. 2 shows a comparison of the deduced amino acid sequence of the mouse XPC (mXPC) protein (SEQ ID NO:1) from part of a single large exon in the mouse xpc genomic locus, which is located at the 3' end of the 3' holomology region shown in FIG. 1, with that of the corresponding deduced amino acid sequence of the human XPC (hXPC) protein (SEQ ID NO:2).

In FIG. 5, (□) represents +/+ wild-type primary embryonic fibroblasts, and (■) represents $xpc^{m1}/xpc^{m1}$ cells.

In FIG. 6, (□) represents +/+ wild-type primary embryonic fibroblasts, and (■) represents $xpc^{m1}/xpc^{m1}$ cells.

In FIG. 7, (□) represents +/+ wild-type primary embryonic fibroblasts, and (■) represents $xpc^{m1}/xpc^{m1}$ cells.

In FIG. 8, (□) represents +/+ wild-type mice, (○) represents $xpc^{m1}/+$ mice, and (■) represents $xpc^{m1}/xpc^{m1}$ cells.

DETAILED DESCRIPTION OF THE INVENTION

Figure 1:
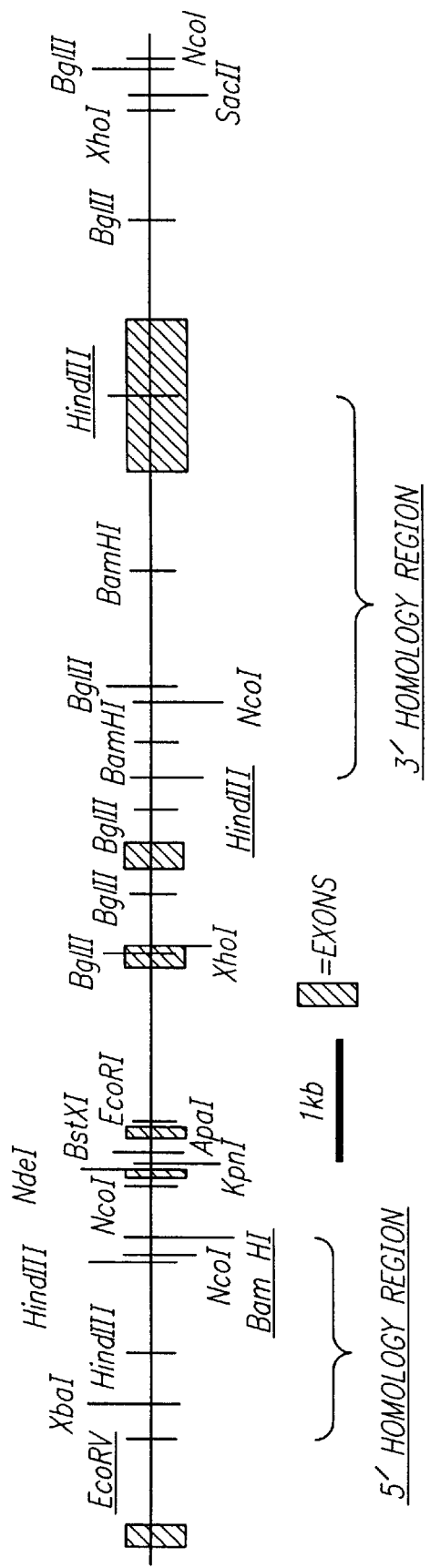
FIG. 1 is a partial restriction map of the genomic locus of the mouse xpc gene useful in the construction of a targeting vector to knockout the xpc gene. The position of putative exons are also shown.

As discussed above, in one embodiment, the above described objects of the present invention have been met by a mouse cell comprising two chromosomal alleles of the xpc gene, wherein at least one of said alleles contains a mutation such that said cell produces less than wild-type levels of XPC activity.

As used herein, XPC-deficient means that at least one of the two wild-type XPC chromosomal alleles has been mutated such that less than wild-type levels of the XPC activity are produced. Thus, XPC-deficient genotypes include a homozygous, as well as a heterozygous genotype, although a homozygous genotype is preferable.

The particular means of measuring XPC activity is not critical to the present invention. XPC activity can be easily measured using several methods. For example, one can measure for a deficiency in XPC mRNA levels by Northern analysis (Sambrook et al, *Molecular Cloning, A Laboratory Manual,* Vol. 1–3, (1989)), or by using a reverse transcriptase polymerase chain reaction (RT PCR) (Sambrook et al, supra). Alternatively, one can measure protein levels of XPC by Western Blot (Sambrook et al, supra) using an antibody to XPC protein.

The mutation in the xpc gene is preferably a deletion mutation, although substitution mutations and/or insertion mutations are also included within the scope of the present invention. The mutants of the present invention preferably lack part of the DNA sequence coding for XPC so that a defective xpc allele is more likely made.

Deletion mutations can be introduced within the xpc gene taking advantage of the convenient restriction sites therein, such as any of the exonic BglII or HindIII restrictions sites or other sites which are easily identified by exonic sequencing of the xpc gene and restriction mapping (see FIG. 1), and the techniques described by Hasty et al, *Mol. Cell. Biol.,* 11:4509–4517 (1991); and Joyner et al, *Nature,* 338:153–156 (1989).

Substitution mutations can be prepared by site-directed mutagenesis, as described by Hasty et al, *Nature,* 350:243–246 (1991), so as to introduce a stop codon or other mutation near the 5' end of the xpc gene so as to give rise to abortive production of XPC protein or production of a mutant protein of deficient XPC activity.

Insertion mutations can be introduced within the xpc gene taking advantage of the convenient restriction sites therein, such as any of the exonic BglII or HindIII restrictions sites or other sites which are easily identified by exonic sequencing of the xpc gene and restriction mapping (see FIG. 1), and the techniques described by Hasty et al, *Mol. Cell. Biol.,* 11:4509–4517 (1991); and Joyner et al, *Nature,* 338:153–156 (1989).

Another method of introducing a mutation in the xpc allele consists of infecting cells with a retrovirus which integrates in the xpc locus, using the techniques described by von Melchner et al, *Genes & Dev.,* 6:919–927 (1992); Friedrich et al, *Genes & Dev.,* 5:1513–1523 (1991); and Friedrich et al, *Methods in Enzymology,* 225:681–701 (1993), thereby creating a mutated xpc allele.

The coding region of the xpc gene is approximately 2500 bp in size. Deletion mutants can be produced by eliminating a DNA fragment from a coding region of the xpc gene so that proper folding or substrate binding of the XPC protein is prevented. The size of the deletion may vary, but in general a larger deletion, is preferable to a smaller deletion, since the larger deletions are more likely to result in a greater deficiency in XPC activity. Alternatively, deleting a single base pair or two base pairs or any number of base pairs not divisible by 3 from the coding region will result in a frame-shift mutation which will be deleterious to making a functional XPC protein. In the latter instance, a truncated polypeptide may be produced because polypeptide synthesis is aborted due to a frame-shift-induced stop codon. Still, changing a single base pair in the coding region of the xpc gene which results in an amino acid change can alter the proper folding of the XPC protein, and thereby create an XPC-deficiency. A single amino acid change so generated can also alter the affinity of XPC for its substrate, and thereby result in a deficiency of XPC activity.

The preferred size of the deletion is about several hundred nucleotides near the 5' end of the gene. Preferably, such a deletion will eliminate a number of nucleotides from the coding region not evenly divisible by 3, thereby creating a frame-shift mutation as well.

The mouse cells of the present invention can be prepared by the following steps:

(1) Constructing a targeting vector comprising a cloning vector and a DNA fragment containing at least one positive selectable marker gene flanked by two contiguous region of the mouse xpc gene or genomic locus which are in the same 5' to 3' orientation to one another (in the case of substitution mutants or insertions mutants) or non-contiguous regions of the mouse xpc gene or genomic locus which are in the same 5' to 3' orientation to one another (in the case of deletion mutants);

(2) Transfecting xpc⁺ mouse cells with the targeting vector of step (1);

(3) Screening or selecting for said marker in the resulting transfected mouse cells of step (2); and (4) Screening for XPC-deficient mouse cells from those cells in step (3) which are found to contain or express said marker.

The target vector of step (1) may also include a negative selectable marker gene adjacent to one of the non-contiguous regions. This negative selectable marker can increase the likelihood of recovering the desired homologous recombination event, i.e., mutation in the xpc gene.

The precise xpc gene or genomic locus sequences which must be present in the targeting vector of step (1) will depend on the site chosen for the insertion or the sequences chosen for the substitution or deletion, and (2) the restriction nucleases to be employed in the engineering of the insertion or deletion mutants.

The specific contiguous regions (hereinafter referred to as "regions of homology") required in step (1) depend on the specifics of the insertion or substitution in the targeting vector. Similarly, the specific non-contiguous regions (also hereinafter referred to as "regions of homology") required in step (1) depend on the specifics of the deletion in the targeting vector. In general, the size of the regions of homology used in the targeting vector will be at least about 400 bp, although longer or shorter regions can be used. In general, it is preferable to use regions of homology of approximately 1.5 kb or greater to insure a high degree of targeting efficiency. In the targeting vector described in detail in FIG. 3, the 5' and 3' homology regions on both sides of the deletion are 1.8 kb and 3.0 kb in length, respectively.

The size of the insertion may also vary and depends on the regions of homology used in the targeting vector. Generally, the size of the insertion will be about 4.0 kb.

The size of the deletion may also vary and depends on the regions of homology used in the targeting vector. That is, since non-contiguous regions of homology are used in the targeting vector, that region in the wild-type allele which is located between the regions of homology constitutes the region to be deleted upon homologous recombination with the targeting vector. The region deleted in Example 3 below is approximately 4.7 kb in length, although that size is not critical and either more or less can be deleted from the locus and still result in XPC-deficiency. It is preferable that the deletion include at least one exon or a portion of an exon of the xpc gene so as to result in mutant XPC mRNA.

Another alternative is to generate a deletion or other mutation in the non-coding splicing region of the xpc gene which affects the proper splicing of the XPC mRNA. Such a mutation can create a mutant XPC transcript which is missing an entire exon or several exons as compared to the wild-type XPC mRNA.

Another alternative is to delete a non-coding regulatory region to decrease expression of the xpc gene.

Figure 3:
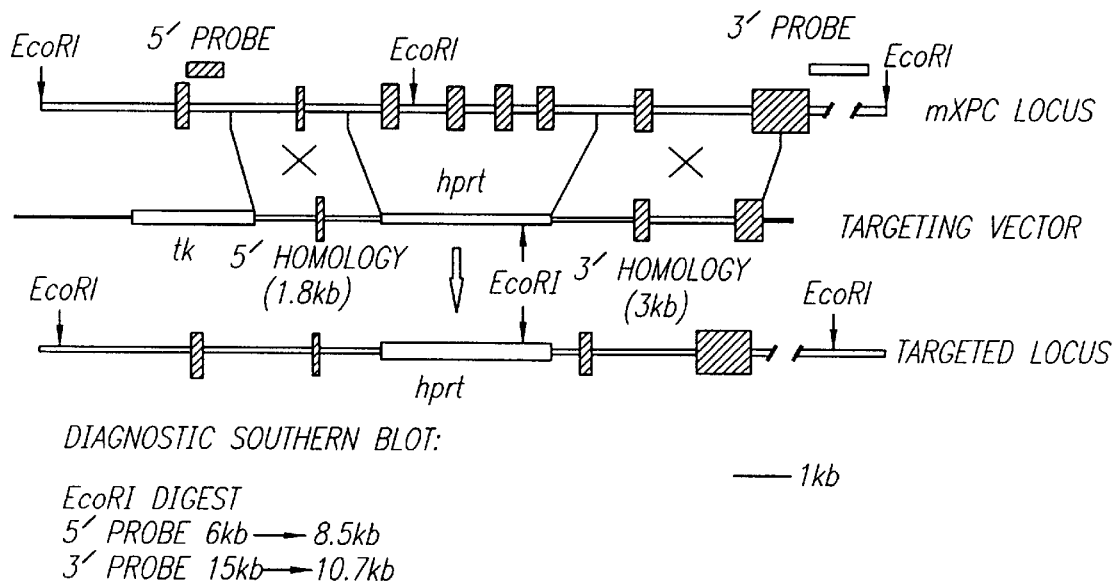
FIG. 3 illustrates the homologous recombinational event between the targeting vector, containing a mutation in the xpc gene, as well as a tk gene and a hprt gene; and the mouse xpc genomic locus used in Example 3 below to facilitate the production of XPC-deficient mouse cells. The position of putative exons is also shown.

The particular positive and negative selectable markers employed in the present invention are not critical thereto. Examples of preferred positive and negative selectable markers are listed in Table 1 below. The positive selectable marker should be located between the regions of homology, and the negative marker, if one is used, is preferably located outside of the regions of homology, either 5' or 3' to those regions as shown in FIG. 3. The regions of homology are preferably in the same 5' to 3' orientation to one another while the orientation of the positive and negative selectable markers are not critical.

TABLE 1

Selectable Markers for Use in Gene Targeting

| Gene | Type | Selective Agents | Preferred Concentration of Selective Agent | Organism |
| --- | --- | --- | --- | --- |
| neo | + | G418 | 50–1000 μg/ml | Eukaryotes |
| hyg | + | Hygromycin | 10–1000 μg/ml | Eukaryotes |
| hisD | + | Histidinol | 5–500 μg/ml | Animals |
| gpt | + | Xanthine | 50–500 μg/ml | Animals |
| hprt | + | Hypoxanthine | 0.01–10 mM | All |
| HSV-tk | – | Gancyclovir | 0.05–200 μM | Animals |
| | – | FIAU | 0.02–100 μM | Animals |
| hprt | – | 6-thioguanine | 0.1–100 μg/ml | All |
| gpt | – | 6-thioxanthine | 0.1–100 μg/ml | Animals |
| Diptheria toxin | – | None | None | Animals |
| Ricin Toxin | – | None | None | Animals |

TABLE 1-continued

Selectable Markers for Use in Gene Targeting

| Gene | Type | Selective Agents | Preferred Concentration of Selective Agent | Organism |
| --- | --- | --- | --- | --- |
| cytosine deaminase | – | 5-fluorocytosine | 10–500 μg/ml | All |

Positive and/or negative selectable marker genes are functional in the transfected cells if the phenotype expressed by the DNA sequences encoding such selectable markers is capable of conferring either a positive or negative selectable characteristic for the cell that is expressing the sequence.

The positive selectable marker is preferably engineered to be functional in the transformed cells in which the gene targeting is being performed. The means by which the positive selectable marker gene is made functional is not critical to the present invention. Positive selection is accomplished by exposing the cells to an appropriate agent which kills or otherwise selects against cells not containing an integrated positive selectable marker. Examples of such agents are listed in Table 1 above. The positive selectable marker gene may have a promoter driving its expression (Donehower et al, *Nature,* 356:215–21 (1992)), or it may be driven by the juxtaposition of transcriptional elements at the target locus with the positive selectable marker (Le-Mouellic et al, *Proc. Natl. Acad. Sci., USA,* 87:4712–4716 (1990); and Mansour et al, *Proc. Natl. Acad. Sci., USA,* 87:7688–7692 (1990)). This latter method requires that the transcriptional elements be active in the transformed cells.

If a negative selectable marker is included in the targeting vector, it should be functional in the transformed cells and it may be located either 5' or 3' to the regions of homology. Its transcriptional orientation relative to the regions of homology is not important.

The mutation engineered in the targeting vector can contain DNA sequences between the regions of homology, in addition to a positive selectable marker, e.g., an oligonucleotide linker, in place of the deleted xpc DNA. The oligonucleotide linker is generally 8–10 nucleotides in length, but can be longer, e.g., about 50 nucleotides, or shorter, e.g. 4, 5 or 7 nucleotides. The preferred length of the oligonucleotide linker is about 20 to 40 nucleotides in length. The DNA sequence of the oligonucleotide linker is not critical.

The method of inserting the oligonucleotide between the regions of homology in the targeting vector DNA will depend upon the type of oligonucleotide linker used. Palindromic double stranded linkers containing one or more restriction nuclease sites in the oligonucleotide sequence (New England Biolabs) may be inserted by well-known procedures (Maniatis et al, *Molecular Cloning,* Cold Spring Harbor Laboratory (1982)). Oligonucleotide linkers may also be inserted into deletions in plasmid DNA by tailing ends with complementary homopolymers using terminal transferase (Maniatis et al, supra). Alternatively, an oligonucleotide linker may be inserted into a deletion in a plasmid by bridging, through annealing of oligonucleotide containing ends complementary, to a cleaved plasmid's 5'-recessed and 3'-protruding cohesive ends, followed by filling in of the gap complementary to the oligonucleotide sequence with DNA polymerase (Klenow fragment). After subsequent ligation with T4 DNA ligase, closed circular DNA molecules can be regenerated. If the targeting vector is designed such that the deleted region interrupts an exon, by the judicious choice of oligonucleotide linker length and sequence, frameshift mutations and/or stop codons may be produced in the mouse xpc gene, augmenting the effect of deletions within the mouse xpc gene.

The mutation engineered in the targeting vector can contain DNA sequences between the regions of homology in addition to the positive selectable marker, e.g., splice acceptor sequences. Such sequences have been shown to facilitate aberrant splicing to create mutant message (Friedrich et al, Genes & Dev., 5:1513–1523 (1991)).

The DNA used as regions of homology is preferably derived from genomic DNA of the mouse xpc genomic locus. The strain of mouse from which the DNA is derived is not critical to the present invention, but preferably it should be the same as the strain of mouse from which the cells in which the gene targeting will be performed, are derived. Using DNA for the regions of homology which is isogenic to the cells in which the gene targeting is performed may enhance the efficiency with which gene targeting is accomplished (te Riele et al, Proc. Natl. Acad. Sci., USA, 89:5128–5132 (1992)).

The regions of homology may be derived from genomic libraries of mouse DNA which may be cloned into a variety of library vectors, such as lambda phage vectors, cosmid vectors, plasmid vectors, p1 phage vectors, yeast artificial chromosome vectors, or other vectors (Sambrook et al, supra). The regions of homology to be used in the targeting vector can also be derived directly from genomic DNA using the polymerase chain reaction (PCR). This method can rely on knowledge of the published sequence of the human xpc gene (Legerski et al, Nature, 359:70–73 (1992)). The regions of homology so derived can be subcloned directly into the targeting vector.

The particular cloning vector employed in the present invention to construct the targeting vector comprising the regions of homology separated by a positive selectable marker gene and an optional flanking negative selectable marker is not critical, as long as the cloning vector contains a gene coding for a selective trait, e.g., drug resistance. Examples of such cloning vectors include pBR322 and pBR322-based vectors (Sekiguchi et al, Gene, 21:267 (1983)), pMB9, pBR325, pKH47 (Bethesda Research Laboratories), pBR328, pHC79, phage Charon 28 (Bethesda Research Laboratories, Boehringer Mannheim Biochemicals), pKB11, pKSV-10 (P-L Biochemicals), pMAR420 (Otsuka et al, Virol., 113:196 (1981)), oligo (dG)-tailed pBR322 (Bethesda Research Laboratories), pBluescript or similar plasmids (Stratagene), puc19 or similar plasmids (New England Biolabs).

Alternatively, the targeting vector comprising the regions of homology separated by a positive selectable marker gene and an optional flanking negative selectable marker can be cloned into other cloning vectors, such as such as lambda phage vectors, cosmid vectors, plasmid vectors, p1 phage vectors, yeast artificial chromosome vectors, or other vectors (Sambrook et al, supra).

Another option is to prepare the components of the targeting vector synthetically by PCR, and simply ligate each component into its proper position by choosing restriction endonuclease sites for ligation which insure proper orientation of the regions of homology relative to each other, and to insure that the positive selectable marker is located between the regions of homology.

Other cloning vectors containing unique cloning sites which are useful in the present invention can be determined upon evaluation of restriction nucleases other than EcoRV and BamHI for the 5' homology region and HindIII for the 3' homology region, which were used in the Examples herein (see FIG. 1). Other restriction nucleases which can be employed to produce fragments containing the mouse xpc gene, and thus other cloning vectors which can be useful in the present invention, are readily apparent from the mouse xpc gene restriction map and targeting vector shown in FIGS. 1 and 3, and which are discussed more fully below.

For example, other regions of homology can be derived from restriction digests according to FIG. 1, such as XbaI and HindIII for the 5' homology region and a BglII fragment for the 3' homology region. Similarly, a HindIII-EcoRI fragment can be used for the 5' homology region and a BamHI fragment for the 3' homology region. Many combinations of restriction endonucleases can be used to generate a targeting vector to mutate the xpc gene. These regions of homology can be cloned into any of a large number of commercially available plasmids, such as the pBluescript series (Stratagene), the puc series (New England Biolabs), or the PGEM series (Promega).

The particular method for screening for XPC-deficient mouse cells is not critical to the present invention. For example, XPC-deficient mouse cells can be screened for mutations in the xpc gene, e.g., by Southern blotting using DNA probes for said mutation, or by PCR. In Example 4 below, Southern blotting using a probe 5' to the mutated locus was used to identify cell lines heterozygous for the engineered mutation by the presence of an 8.5 kb mutant DNA fragment and a 6.0 kb wild-type DNA fragment (FIG. 3).

The specific host employed for growing the targeting vectors of the present invention is not critical. Examples of such hosts include E. coli K12 RR1 (Bolivar et al, Gene, 2:95 (1977)); E. coli K12 HB101 (ATCC No. 33694); E. coli MM21 (ATCC No. 336780); and E. coli DH1 (ATCC No. 33849). The preferred host in the present invention is DH5a (Life Technologies). Similarly, alternative vector/cloning systems can be employed, such as targeting vectors which grow in E. coli or Saccharomyces cervisiae, or both, or plasmid vectors which grow in B. subtillis (Ure et al, Methods in Enzymology "Recombinant DNA", Vol. 101, Part C, Academic Press, N.Y. (1983)).

The specific xpc$^+$ mouse cell which is mutated in the present invention is not critical thereto, and is preferably a precursor pluripotent cell. The term precursor means that the pluripotent cell is a precursor of the desired transfected pluripotent cell which is prepared in accordance with the present invention. The pluripotent cell may be cultured in vivo to form a mutant mouse (Evans et al, Nature, 292:154 (1981)). Examples of xpc$^+$ mouse cells which can be employed in the present invention include embryonic stem (ES) cells. Primary isolates of ES cells may also be used, and can be obtained directly from embryos, such as described for the EK.CCE cell line (Evans et al, Nature, 292:292-156 (1981)) or for ES cells in general (Robertson, In: Tetracarcinomas and Embryonic Stem Cells: A Practical Approach, Ed. Robertson, IRL Press, Oxford, pages 71–112 (1987)). The particular ES cell employed in the present invention is not critical thereto. Examples of such ES cells are AB 2.1 and AB 2.2, hprt$^-$ cell lines (Matzuk et al, Nature, 360:313–319 (1992)), and AB 1.0, an hprt$^+$ cell line (McMahon et al, Cell, 62:1073–1085 (1989)). In the present invention, it is preferable to use an hprt$^-$ cell line when the positive selectable marker is an hprt gene. Other selectable markers, such as those outlined in Table 1 can be used in other stem cell lines.

The ES cells are preferably cultured on stromal cells, e.g., STO cells, and/or primary embryonic fibroblast cells, as described by Robertson, supra. The stromal (and/or fibroblast) cells serve to reduce the clonal outgrowth of abnormal ES cells.

In order to obtain the XPC-deficient mice of the present invention, the mutant embryonic stems cells are injected into mouse blastocysts as described by Bradley, In: *Teratocarcinomas and Embryonic Stem Cells: A Practical Approach*, pages 113–151 (1987)).

The particular mouse blastocysts employed in the present invention are not critical thereto. Examples of such blastocysts include those derived from C57BL6 mice, C57BL6 Albino mice, Swiss outbred mice, CFLP mice and MFI mice (Bradley, supra).

Mice heterozygous for the xpc mutant allele generated from the injected blastocyst can be screened for mutations in the xpc gene, e.g., by Southern blotting using DNA probes for said mutation, or by PCR (Sambrook et al, supra). For example, in Example 4 below, Southern blotting using a probe 5' to the mutated locus identified mice heterozygous for the engineered mutation by the presence of an 8.5 kb mutant DNA fragment and a 6.0 kb wild-type DNA fragment (FIG. 3).

The mutant mice of the present invention can be intercrossed to obtain mice homozygous for the mutation in the xpc gene, and/or can be crossed with other mice strains to transfer the xpc mutation into these other strains. For example, as described in Example 4 below, Southern blotting using a probe 5' to the mutated locus identified mice homozygous for the engineered mutation by the presence of only an 8.5 kb mutant DNA fragment and no 6.0 kb wild-type DNA fragment (FIG. 3).

The method for screening for the damaging and tumorigenic effect of ultraviolet light or a chemical DNA damaging agent comprises the steps of:

(1) exposing mouse cells, which produce less than wild-type levels of XPC activity as a result of a mutation in the xpc gene, to UV light or a chemical DNA damaging agent; and (2) evaluating cytotoxicity in the resulting exposed cells.

The particular mouse cells are not critical to the present invention. Examples of such mouse cells include embryonic fibroblasts and skin fibroblasts. Embryonic fibroblasts are the preferred cells to be employed in the present invention because of their high proliferative capacity and high plating efficiencies which allow for rapid experimentation on UV sensitivity.

The amount of exposure to UV is not critical to the present invention, but is typically in a range of incrementally increasing values from 0 $J/m^2$ to 10 $J/m^2$.

The amount of exposure to chemical DNA damaging agents may vary, depending on the particular agent used. The particular chemical DNA damaging agent employed is not critical to the present invention. Examples of such agents include 4-nitroquinoline 1-oxide (4NQO), mitomycin c and bleomycin. The dose of exposure to cells in culture will be in a range to establish a kill curve that reflects the relative sensitivity of the XPC-deficient cells to the various agents. The dose range typically used in such kill curve experiments is between 1.0 and 5.0 $\mu$M for 4NQO, and from 0.2 to 1.6 $\mu$M for mitomycin c and bleomycin.

Cytotoxicity can be evaluated by counting the number of colonies of cells surviving after exposure to the toxic agents.

The method for screening for the damaging and tumorigenic effect of ultraviolet light or a chemical DNA damaging agent comprises the steps of:

(1) exposing skin of a mutant mouse, which produces less than wild-type levels of XPC activity as a result of a mutation in the xpc gene, to UV light or a chemical DNA damaging agent; and (2) evaluating pathology in the resulting exposed mouse.

In this method, the amount of exposure to UV light is not critical to the present invention, but is typically delivered in a range from about 500 to 2500 $J/m^2$, which approximates the amount of sun exposure during 3 to 20 min, depending on clear weather conditions, in Houston, Tex. in July at 2:00 pm.

Pathological changes in the exposed skin can be evaluated visually as tumors, or by histological staining of tissue specimens, as described by Sands et al, *Nature*, 377:166 (1995), which is incorporated by reference herein.

The following examples are provided for illustrative purposes only and are in no way intended to limit the scope of the present invention.

EXAMPLE 1

Cloning of the Mouse xpc Gene

The mouse homologue of the human xpc gene was cloned from a mouse 129-strain genomic library.

More specifically, initially a DNA fragment of the human xpc gene was obtained using a reverse transcriptase polymerase chain reaction (PCR) on RNA obtained from human cells (Sambrook et al, supra). The following oligonucleotide primers were used in the PCR: 5'-GAAGAGAGGGGGTACCATGAATGAAG-3' (SEQ ID NO: 3), and 5'-GAGGAGCCTCCTGGATCCGCAGTC-3' (SEQ ID NO: 4), and were based on the human xpc gene sequence (Legerski et al, *Nature*, 359:70–73 (1992)). The DNA fragment of the human xpc gene so obtained was subcloned into the HindIII site of plasmid vector pBluescript SK+ (Stratagene). A radiolabeled probe was then made using the subcloned DNA fragment of the human xpc gene.

Next, the radiolabelled probe was used to screen a mouse 129-strain genomic lambda phage library (Stratagene) to identify phage containing the homologous mouse gene. Three positive phage were isolated, grown, and restriction mapping was performed on the DNA inserts, as described by Sambrook et al, supra, so to produce a map of the xpc genomic locus (see FIG. 1). One clone containing the mouse xpc genomic locus was designated mXPC clone #9.

Based on the restriction map, putative exons were identified by hybridization with probes from the coding region of the human xpc gene, and selected sequencing was performed (Sambrook et al, supra).

The DNA sequence of a portion of mouse xpc CDNA (SEQ ID NO:5) has substantial DNA sequence similarity to the human xpc gene. That is, 78% identity was found at the nucleotide level.

In the present invention, the human cDNA sequence was used as a probe. However, the mouse cDNA sequence could also be radiolabeled, and used as a probe to clone the genomic locus of the mouse xpc gene for knockout vector construction.

Deduced amino acid comparison was performed using the GAP program in GCG sequence analysis package, version 8, Genetics Computer Group, Madison Wis. One large contiguous coding region (exon), which is bisected by a HindIII site, and identified in the mouse xpc genomic clone in comparison to the deduced amino acid sequence of the human xpc cDNA sequence, is shown in FIG. 2. In FIG. 2, identical amino acids are indicated by a vertical line between the mouse and human sequences, conservative amino acid changes are shown with two dots, and moderately conservative amino acid changes are shown with one dot, using threshold values of 1.5, >0.5, and >0.1, respectively (Gribskov et al, *Nuc. Acids Res.*, 14:6745 (1986)).

The mouse XPC protein was found to have extensive sequence similarity to the human XPC protein. That is, 79% identity was found at the amino acid level between mouse exonic regions and the human XPC CDNA sequence.

EXAMPLE 2

Construction of Targeting Vector

To generate XPC-deficient mice, a targeting vector which contains 1.8 kb of DNA homologous to the 5' end of the mouse xpc gene, and 3.0 kb of DNA homologous to the 3' end of the mouse xpc gene, was constructed (see FIG. 3). This vector also contains a marker for positive selection (the hprt mini-gene) (Matzuk et al, *Nature*, 360:313 (1992)), and a marker for negative selection (the tk gene) (Mansour et al, *Nature*, 226:348 (1988)) (see FIG. 3).

Figure 5:
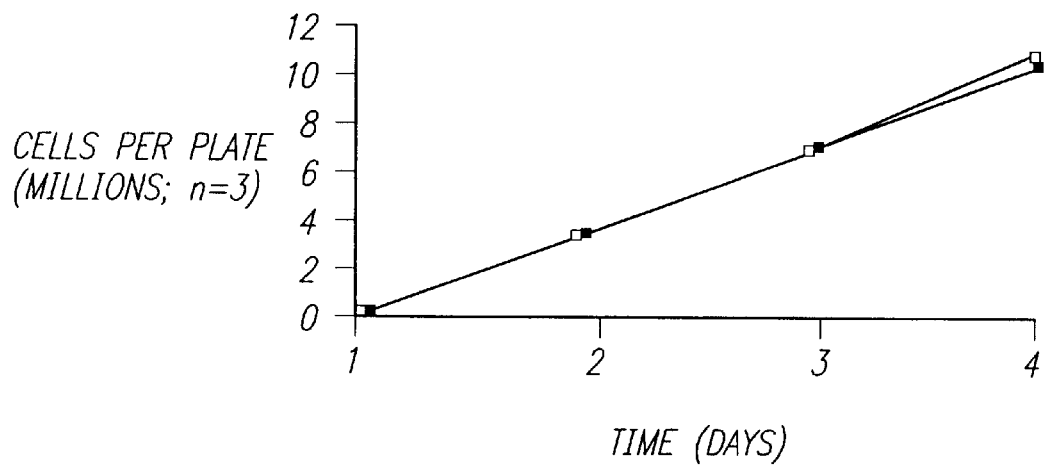
FIG. 5 shows the proliferative ability of XPC-deficient mouse cells.

More specifically, based on the restriction map generated in FIGS. 1, 5' and 3' homology regions were selected. The 5' homology region used was located near the 5' end of the xpc genomic locus and was isolated by EcoRV and BamHI digestion of the phage clone obtained in Example 1 above (the sites are underlined on the restriction map shown in FIG. 1), which produced a DNA fragment of approximately 1.8 kb. For ease of subsequent subcloning steps, this fragment was subcloned into Bluescript SK$^+$ vector (Stratagene) which had been prepared by cutting with XbaI, treating the XbaI end with Klenow fragment and nucleotides to make a blunt end (Sambrook et al, supra), and then cutting with BamHI. This effectively produced a vector that had complementary ends to the insert for directed ligation into the vector.

The 3' homology region was isolated by HindIII digestion of the phage clone obtained in Example 1 above, (the sites are underlined on the restriction map shown in FIG. 1), which produced a DNA fragment of approximately 3.0 kb. For ease of subsequent subcloning steps, the 3' homology region was subcloned into the HindIII site of Bluescript SK$^+$ vector (stratagene). This allowed for a subsequent restriction digestion with EcoRI and SalI to release the entire fragment from the subcloning vector, with the effective change of restriction sites on the ends of the 3' homology to EcoRI and SalI.

Again, the positive selectable marker used was the hprt mini-gene (Matzuk et al, supra), which was digested with BamHI and EcoRI to release a DNA fragment of approximately 3.6 kb containing the marker gene.

To prepare the positive selection targeting vector, the subclone containing the 5' homology region was used as the base vector for inserting the other required elements. The 5' homology vector was digested with BamHI and XhoI. Then, the positive selectable marker was digested to produce sticky ends with BamHI and EcoRI. Next, the 3' homology region subclone was digested with EcoRI and SalI. These three fragments were ligated together in a single directed ligation reaction (FIG. 3).

To prepare the positive-negative selection targeting vector, the negative selectable tk gene (U.S. Pat. No. 5,464, 764) was added upstream of the 5' homology region at the unique NotI site (FIG. 3).

EXAMPLE 3

Transfection of Mouse Embryonic Stem Cells

Homologous recombination of the targeting vector obtained in Example 2 with the xpc genomic locus was effected in mouse embryonic stem cells (see FIG. 3). The ES cell were grown on a feeder layer of STO cells as described by Robertson, supra.

More specifically, 10 Mg of the positive-negative targeting vector obtained in Example 2 above was transfected into $1.0 \times 10^7$ AB 2.1 mouse 129 strain embryonic stem cells (Matzuk et al, *Nature*, 360:313 (1992)), and the resulting cells were grown in HAT (hypoxanthine, aminopterine and thymidine) positive selection media so as to select for those cells which were transfected with the targeting construct. Negative selection against the tk gene was also carried out using the drug FIAU (McMahon et al, *Cell*, 62:1073–1085 (1989)) so as to enhance for selection of those cells which had undergone a homologous recombination event at the xpc locus (Capecchi et al, supra). Surviving colonies were screened by mini-Southern, as described by Ramirez-Solis et al, *In: Guide to Techniques in Mouse Development*, Wassarman et al, Eds., Academic Press, Inc., New York, 225:855 (1993) using fragments of DNA from the xpc locus, which were 5' and 3' to the regions of homology of the targeting vector, as probes so as to detect the double reciprocal homologous recombination event between the targeting vector and the xpc locus in the chromosome of the ES cell. In particular, ES cell genomic DNA for the mini-southern was digested with restriction enzyme EcoRI. The desired recombination event was detected using the 5' probe derived from an EcoRV-EcoRI digestion of the mouse xpc genomic clone as indicated in FIG. 1, which revealed a mutant allele of 8.5 kb as compared to the wild-type allele of 6.0 kb. The desired recombination event was confirmed using the 3' probe derived from an XhoI-HindIII digestion of mouse xpc genomic clone, as indicated in FIG. 1, which revealed a mutant allele of 10.7 kb as compared to the wild-type allele of 15 kb (see FIG. 3) Ten positive ES cells clones were identified as correct replacement events, with an approximate 4.7 kb genomic deletion. The targeting frequency was approximately 1/20. One of the clones was designated ES cell line xpc$^{m1}$-202.

EXAMPLE 4

Generation of XPC-deficient Mice

10–30 cells from ES cell clone xpc$^{m1}$-202 obtained in Example 3 above were injected into C57BL6 Albino host blastocysts as described by Bradley, supra. The resulting injected blastocysts were implanted into pseudopregnant females and chimeric offspring were born, as demonstrated by a mixture of agouti and albino coat colors (agoutic contribution from the ES cell line and albino from the wild-type host embryos) (Bradley, supra). Chimeric male mice were mated to wild-type C57BL6 Albino females, and agouti pups were born, indicating successful germline transmission of the ES cell component of the chimeric mouse, and resulting in C57BL6 Albino/129 hybrids (referred to as C567BL6/129 hybrids). At three weeks of age, the offspring from the chimeric crosses were screened for the mutant xpc allele as described below.

Genomic DNA was isolated from the resulting mice as described by Sambrook et al, supra. Then, 10 μg of the resulting genomic DNA was digested with EcoRI, and subjected to Southern blot analysis using the 5' and 3' probes as described above for the mini-Southerns. ES cell clone xpc$^{m1}$-202 was found to have transmitted the mutant allele through the germline having an approximate deletion of 4.5 kb.

A male and female mouse were identified as heterozygous for the mutant allele, and then intercrossed. The chimeric mouse which had demonstrated germline transmission was also crossed with a wild-type 129 strain mouse, in order to place the mutant allele on the 129 strain background. Genomic DNA was isolated from the resulting mice, and 10 μg of the genomic DNA was digested with EcoRI, and subjected to Southern blot analysis, using the 5' and 3' probes described above. A single 6.0 kb band indicated a +/+ animal, a single 8.5 kb band indicated an animal homozygous for the targeted mutant allele ($xpc^{m1}/xpc^{m1}$). The presence of both bands indicated a heterozygous animal ($xpc^{m1}/+$).

Several mating pairs of heterozygous ($xpc^{m1}/+$) mice were intercrossed to obtain homozygous ($xpc^{m1}/xpc^{m1}$) mice. Of 150 offspring from ($xpc^{m1}/+$) intercrosses, 25% were +/+, 46% ($xpc^{m1}/+$) and 29% ($xpc^{m1}/xpc^{m1}$), approximating the expected Mendelian ratios. This result indicated that there is no developmental selection against the mutant allele in heterozygous or homozygous mutant embryos. The $xpc^{m1}/xpc^{m1}$ mice were viable and fertile, and no difference was noted in behavior or continued viability over a 1.5-year period of monitoring a population of approximately 100 wild-type, ($xpc^{m1}/+$), and ($xpc^{m1}/xpc^{m1}$) mice.

EXAMPLE 5

XPC Activity in Primary Embryonic Fibroblasts

Wild-type and $xpc^{m1}/xpc^{m1}$ primary embryonic fibroblasts were generated to measure XPC activity.

More specifically, mRNA was obtained using the Quick-Prep Micro mRNA purification kit (Pharamacia) from mouse embryonic fibroblasts that were isolated from 13.5 day embryos derived from wild-type and $xpc^{m1}/xpc^{m1}$ mice as described by Harvey et al, *Oncogene*, 8:2457–2467 (1993). Then, 1.2 μg of the mRNA was used to make 1st strand cDNA using oligo dT primers (Superscript RT II kit, Gibco BRL). PCR was then carried out using the following xpc primers 5'-GCTGCAGTGATCCAGGGGAC-3' (SEQ ID NO:6); and 5'-TGGACGGTTCAAAGTCAGAG-3' (SEQ ID NO:7). The PCR conditions were 93° C. for 40 sec, 72° C. for 1 min 30 sec for 34 cycles.

Figure 4:
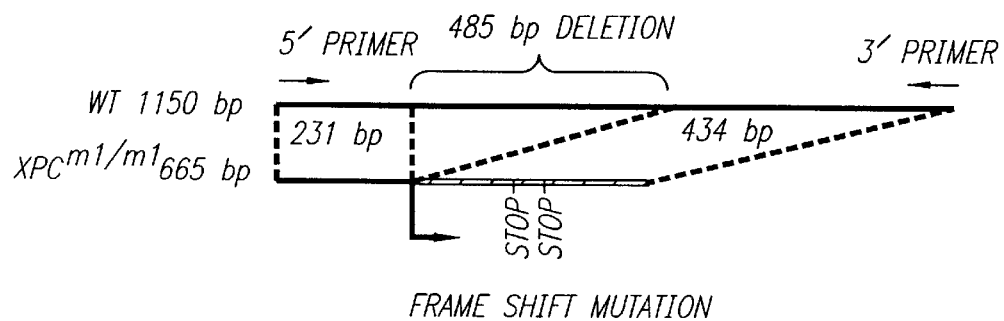
FIG. 4 shows the mutant xpc mRNA which is made as a result of the mutation in the xpc gene described in Example 3. The mutation causes a frame-shift which results in stop codons in the reading frame of the XPC mRNA which in turn results in less than wild-type levels of XPC mRNA in $xpc^{m1}/xpc^{m1}$ cells.

The RT-PCR for XPC mRNA from $xpc^{m1}/xpx^{m1}$ and wild-type embryonic fibroblasts revealed a predicted 1150 bp fragment with wild-type mRNA as template and a 665 bp fragment with mRNA from mutant cells (FIG. 4). Southern blotting with the exonic xpc probe described in Example 3, which was outside of the deleted region indicated that the wild-type and mutant RT-PCR products recovered were, in fact, derived from XPC mRNA.

RT-PCR positive controls using primers to the Mgf gene, i.e., 5'-AGCTGCAGCTGGATCGCAGCGCTGCCTTTCC-3' (SEQ ID NO:8); and 5'-TCGAGCTCTGTTGATACGTCCACAATTACACCTC-3' (SEQ ID NO:9) (Anderson et al, *Cell*, 63:235–241 (1990)), indicated that the reaction conditions were optimized for both wild-type and mutant mRNA templates.

The PCR products obtained with the xpc primers were subcloned into a T-Vector (Promega) and sequenced. The sequencing results of the mutant and wild-type bands revealed a 485 bp deletion in the mutant mRNA resulting in a frameshift mutation and stop codons 151 bp downstream from the deletion point (FIG. 4).

EXAMPLE 6

In vitro Sensitivity of Primary Embryonic Fibroblasts

Wild-type and $xpc^{m1}/xpc^{m1}$ primary embryonic fibroblasts were generated to measure the effect of the $xpc^{m1}/xpc^{m1}$ genotype on the sensitivity of cultured cells to DNA damaging agents, i.e., UV irradiation and 4-nitro-quinoline 1 oxide. Before UV irradiation, the proliferation of the XPC-deficient and wild-type fibroblasts were compared. As shown in FIG. 5, in the absence of UV irradiation, no differences were apparent in the proliferation between the two genotypes.

A. UV Irradiation Colony Survival Assay

More specifically, primary embryonic fibroblasts were isolated from 13.5 day embryos derived from a cross of $xpc^{m1}/+$ mice as described by Harvey et al, supra. Then, cell lines having the $xpc^{m1}/xpc^{m1}$ and +/+genotypes were plated at a low density, i.e., approximately 20,000 cells per 100 mm tissue culture plate, and exposed to increasing doses of UV light using a short wavelength (maximal emission approximately 250 nM–280 nM). The doses used were from 0 J/m$^2$ to 10 J/m$^2$. After UV exposure, the cells were incubated for 10 days in DMEM supplemented with 15% (v/v) fetal calf serum and the antibiotics streptomycin sulfate (50 μg/ml) and penicillin G (50 units/ml), in order to allow for colony formation. The colonies were then fixed in 70% (v/v) ethanol, and stained with methylene blue. The average number of colonies per plate of three independent cell lines of each genotype was calculated for each UV dose; standard deviation (bars) and statistical significance were determined (t test). The results are shown in FIG. 6.

Figure 6:
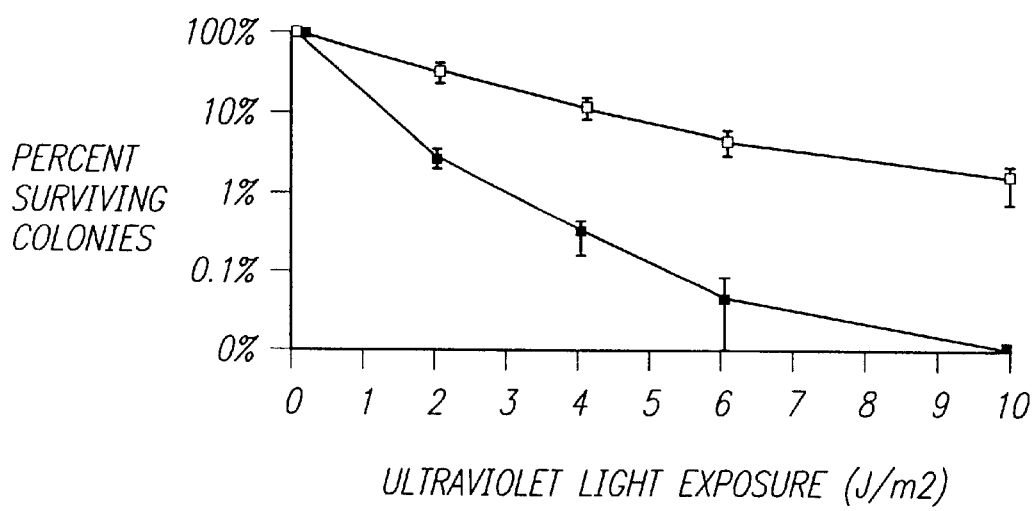
FIG. 6 shows the cytotoxic effects on XPC-deficient mouse cells after exposure to UV light in a colony survival assay.

As shown in FIG. 6, in the absence of DNA damaging agents, i.e., UV irradiation, $xpc^{m1}/xpc^{m1}$ cells were able to proliferate in culture as rapidly as +/+ wild-type cells, and their plating efficiencies were comparable. However, as shown in FIG. 6, upon exposure to UV light, $xpc^{m1}/xpc^{m1}$ cells demonstrated a significantly decreased ability to form colonies compared to wild-type cells (p<0.01, bars represent standard deviation). Embryonic fibroblasts heterozygous for the mutant allele, i.e., $xpc^{m1}/+$ cells, could not be distinguished from wild-type cells, i.e., +/+ cells, in this assay.

Thus, cells homozygous for the mutant allele demonstrated a marked sensitivity to UV light in a colony survival assay, consistent with data from cells derived from XPC patients, which demonstrate a deficiency in "global genome" NER (Venema et al, *Mol. Cell. Biol.*, 11:4128 (1991)).

B. 4-nitro-quinoline 1 oxide Colony Survival Assay

Next, the sensitivity of the primary embryonic fibroblasts to 4-nitro-quinoline 1 oxide (4NQO), an agent known to be a mutagen which acts principally at guanine residues (Galiegue-Zouitina et al, *Carcinogen.*, 10:1961 (1989)), was evaluated.

More specifically, primary embryonic fibroblasts were isolated from 13.5 day embryos derived from a cross of $xpc^{m1}/+$ mice as described by Harvey et al, supra. Then, cell lines having the $xpc^{m1}/xpc^{m1}$ and +/+ genotypes were plated at a low density, i.e., approximately 20,000 cells per 100 mm tissue culture plate, and exposed to increasing doses of 4NQO ranging from 0 μM to 0.8 μM. After 4NQO exposure, the cells were incubated for 10 days in DMEM supplemented with 15% (v/v) fetal calf and the antibiotics streptomycin sulfate (50 μg/ml) and penicillin G (50 units/ml), in order to allow for colony formation. The colonies were then fixed in 70% (v/v) ethanol, and stained with methylene blue. The average number of colonies per plate of three independent cell lines of each genotype was calculated for each UV dose; standard deviation (bars) and statistical significance were determined (t test). The results are shown in FIG. 7.

Figure 7:
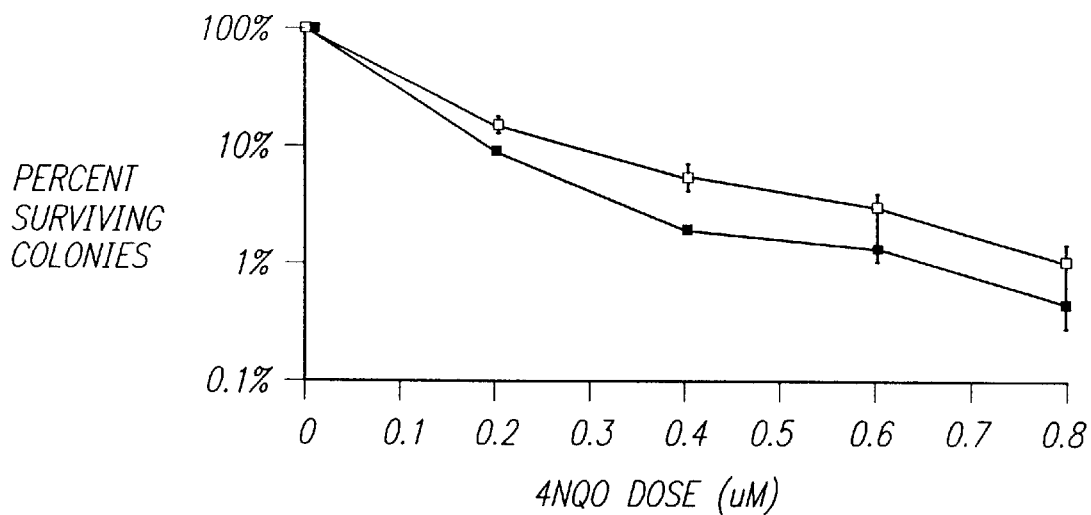
FIG. 7 shows the results of DNA damage in XPC-deficient mouse cells after exposure to the genotoxic agent 4NQO in a colony survival assay.

As shown in FIG. 7, the sensitivity of the $xpc^{m1}/xpc^{m1}$ primary embryonic fibroblasts to 4NQO was not found to be statistically significant (t test) at the dose points tested, compared to the +/+ wild-type cells.

Thus, XPC-deficiency significantly altered cell survival in response to the type of damage caused by UV light, but not that associated with 4NQO exposure.

EXAMPLE 7

In vivo Sensitivity of Mice

The in vivo sensitivity of $xpc^{m1}/xpc^{m1}$, $xpc^{m1}/+$, and $+/+$ litter mates to UV-induced tumorigenesis was evaluated.

More specifically, 8–12 week-old mice were exposed to an average of 2500 J/m² per day (suberythemic dose, maximal emission in the UVB wavelength range) for a 20 week period. The mice were shaved once per week during the 20 week exposure period, and were observed regularly for pathologic changes in the skin. Lesions that were identified grossly as tumors were noted. Histopathologic confirmation of carcinomas was obtained after the animals were sacrificed by placing tissue specimens in neutral buffered 10% (v/v) formalin, and embedding in paraffin. 5.0 μm sections were stained with hematoxylin and eosin by conventional methods. The time to tumor formation is shown in FIG. 8.

Figure 8:
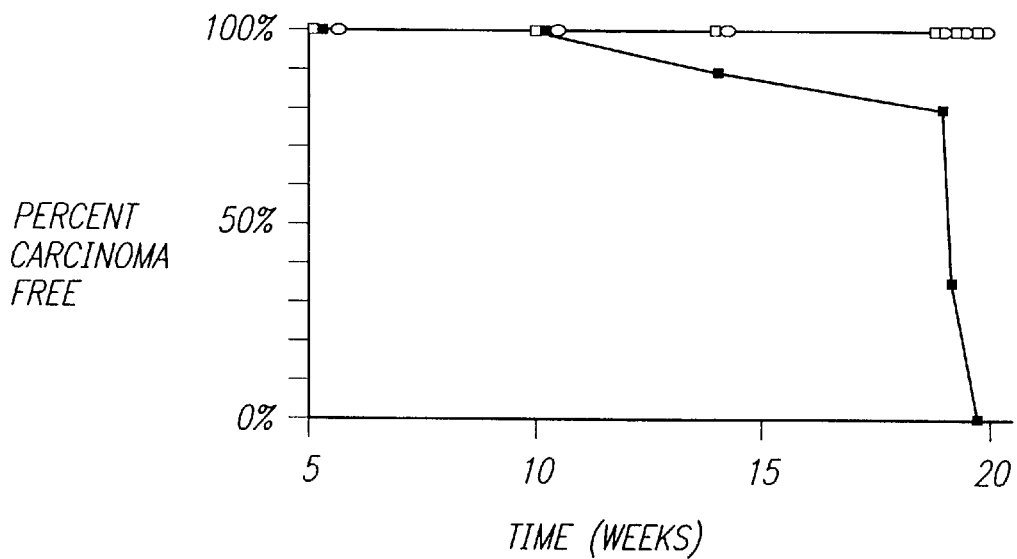
FIG. 8 shows the time to tumor formation in XPC-deficient mice chronically exposed to UV light.

As shown in FIG. 8, $xpc^{m1}/xpc^{m1}$ (n=9) mice demonstrated a rapid induction of skin carcinomas after daily exposure to UV light as compared to $xpc^{m1}/+$ (n=8) and $+/+$ (n=8) litter mates. After 10 days of treatment, all of the $xpc^{m1}/xpc^{m1}$ mice (n=9) exhibited a marked atrophy of the ears while the $xpc^{m1}/+$ mice (n=8) and the $+/+$ mice (n=8) controls appeared normal. At the end of the 20 week exposure, all of the $xpc^{m1}/xpc^{m1}$ mice had developed at least one skin carcinoma, which was confirmed by histologic sections. The results of the histology are summarized in Table 2 below.

TABLE 2

UV-induced Skin Neoplasia in XPC-deficient Mice

| Mouse | Location of Lesion | Histopathology |
|---|---|---|
| 9 | Ear | WD SCC |
|   | Dorsum | WD SCC (3) |
|   |   | MD SCC (2) |
| 11 | Ear | WD SCC, MD SCC |
| 12 | Ear | WD SCC, Papilloma |
| 14 | Ear | Carcinoma *in situ*, WM SCC |
|   | Dorsum | WD SCC, MD SCC |
| 23 | Ear | Papilloma, WD SCC |
|   | Eye lid | MD SCC |
| 24 | Ear | MD SCC |
| 28 | Ear | WD SCC (2) |
|   | Dorsum | WD SCC (3) |
| 188 | Ear | Papilloma (2), WD SCC |
|   | Eye lid | WD SCC |
| 191 | Ear | WD SCC, MD SCC |
|   | Dorsum | MD SCC |

WD SCC = Well Differentiated Squamous Cell Carcinoma
MD SSC = Moderately Differentiated Squamous Cell Carcinoma
The numbers in parentheses indicate the number of lesions identified in a survey of histologic sections.

Mice heterozygous for the mutant xpc allele and wild-type controls did not develop any tumors by the end of the treatment regimen. In addition to these neoplastic lesions, the histologic examination of the skin of the UV irradiated $xpc^{m1}/xpc^{m1}$ mice showed marked hyperplasia of the epidermis, with focal areas of hyperkeratosis and varying degrees of dysplasia, acantholysis and/or dyskeratosis. These lesions have been previously described in UV-irradiated hairless mice (Gallagher et al, *J. Invest. Denn.*, 83:169 (1984)), and are similar to the human lesion known as actinic or solar keratosis (Lever et al, *In: Histopathology of the Skin*, J. B. Lippincott Company, Philadelphia, pp. 523–577 (1990); and Hurt et al, *In: Pathology of Incipient Neoplasia*, Henson et al, Eds., W. B. Saunders Company, Philadelphia, 28:8 (1993)). The skin of XPC-deficient mice also displayed ulcerative and degenerative changes including marked alterations of pigmentation of the epidermis and derinis. In addition, UV treatment produced frequent abnormalities in eyes of $xpc^{m1}/xpc^{m1}$ mice; histologic sections revealed severe keratitis and comeal ulceration. The $+/+$ and $xpc^{m1}/+$ mice showed only moderate hyperplasia in the skin, and infrequent cases of mild keratitis during the UV treatment regimen. Four weeks after the UV treatment regimen was completed, one of $+/+$ mice developed a spindle cell tumor and one of the $xpc^{m1}/+$ mice developed a papilloma. A colony of $xpc^{m1}/xpc^{m1}$, $xpc^{m1}/+$ and $+/+$ mice ranging from 8–12 months of age which were not exposed to a regimen of UV irradiation did not demonstrated any signs of tumor formation or any other pathologic changes.

Mice homozygous for the xpc mutant allele ($xpc^{m1}/xpc^{m1}$) were viable, and did not exhibit an increased susceptibility to spontaneous tumorigenesis at one year of age. However, $xpc^{m1}/xpc^{m1}$ mice were found to be highly susceptible to UV-induced carcinogenesis as compared to mice heterozygous for the mutant allele ($xpc^{m1}/+$) and wild-type controls. This is consistent with XPC patients who are predisposed to skin tumor formation in UV exposed areas of the body (Cleaver, *In: The Metabolic Basis of Inherited Disease*, McGraw Hill, New York (1995)). $xpc^{m1}/xpc^{m1}$ mice also display a spectrum of UV exposure-related pathologic skin and eye changes consistent with the human disease XPC, and confirming their applicability as a mouse model for XPC.

While the invention has been described in detail, and with reference to specific embodiments thereof, it will be apparent to one of ordinary skill in the art that various changes and modifications can be made therein without departing from the spirit and scope thereof.

What is claimed:

1. An isolated mouse cell comprising a mutation in both alleles of the xpc gene, said mutation deleting at least about 4 kilobases of the xpc gene resulting in said cell having greater susceptibility to ultraviolet light damage than a wild-type mouse cell.

2. The isolated mouse cell of claim 1, which is selected from the group consisting of an ES cell and a fibroblast.

3. An isolated mouse cell comprising a mutation in both alleles of the xpc gene, said mutation disrupting exons 3, 4, 5, or 6 of the xpc gene, resulting in said cell being at least about 20 times more sensitive to ultraviolet light damage than a wild-type mouse cell when exposed to about 2 to about 6-Joule per square meter of ultraviolet light.

4. The isolated mouse cell of claim 3, which is selected from the group consisting of an ES cell and a fibroblast.

5. An isolated mouse cell comprising a mutation in both alleles of the xpc gene, said mutation deleting at least about 4 kilobases of the xpc gene, wherein said mutation is upstream of exon 10 of the xpc gene resulting in said cell having greater susceptibility to ultraviolet light damage than a wild-type mouse cell.

6. The isolated mouse cell of claim 5, which is selected from the group consisting of an ES cell and a fibroblast.

7. A mouse comprising a mutation in both alleles of the xpc gene, said mutation deleting at least about 4 kilobases of the xpc gene resulting in said mouse having greater susceptibility to ultraviolet light damage than a wild-type mouse.

8. A mouse comprising a mutation in both alleles of the xpc gene, said mutation disrupting exons 3, 4, 5, or 6 of the xpc gene, wherein said mutation renders embryonic fibroblasts from said mouse at least about 20 times more sensitive to ultraviolet light damage than embryonic fibroblasts from a wild-type mouse when exposed to about 2 to about 6 Joule per square meter of ultraviolet light.

9. A method of screening for the damaging effect of ultraviolet light on a mouse cell comprising the steps of
    (a) exposing a isolated mouse cell, comprising a mutation in the xpc gene, to ultraviolet light, said mutation deleting at least about 4 kilobases of each allele of the xpc gene and said cell having greater susceptibility to ultraviolet light damage than a wild-type mouse cell; and
    (b) evaluating said damaging effect in the mouse cell.

10. The method of claim 9 wherein said isolated cell is selected from the group consisting of an ES cell and a fibroblast.

11. A method of screening for the damaging effect of ultraviolet light on a mouse cell comprising the steps of
    exposing an isolated mouse cell comprising a mutation in both alleles of the xpc gene, to ultraviolet light, said mutation disrupting exons 3, 4, 5, or 6 of the xpc gene and rendering said cell at least about 20 times more sensitive to ultraviolet light than a wild-type mouse cell when exposed to about 2 to about 6 Joule per square meter of ultraviolet light; and
    (b) evaluating said damaging effect in the mouse cell.

12. The method of claim 11 wherein said isolated cell is selected from the group consisting of an ES cell and a fibroblast.

13. A method of screening for the damaging effect of ultraviolet light on a mouse comprising the steps of
    (a) exposing a mouse, comprising a mutation in the xpc gene, to ultraviolet light, said mutation deleting at least about 4 kilobases of each allele of the xpc gene resulting in said mouse having greater susceptibility to ultraviolet light damage than a wild-type mouse cell; and (b) evaluating said damaging effect in the mouse.

14. A method of screening for the damaging effect of ultraviolet light comprising the steps of (a) exposing a mouse comprising a mutation in both alleles of the xpc gene, to ultraviolet light, said mutation disrupting exons 3, 4, 5, or 6 of the xpc gene, and rendering embryonic fibroblasts from said mouse at least about 20 times more sensitive to ultraviolet light damage than embryonic fibroblasts from a wild-type mouse when exposed to about 2 to about 6 Joule per square meter of ultraviolet light; and (b) evaluating said damaging effect in the mouse.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 211 amino acids
      (B) TYPE: amino acid -continued (D) TOPOLOGY: linear (ii) MOLECULE TYPE: protein (xi) SEQUENCE DESCRIPTION: SEQ ID NO: 1:

```
Gln Gly Arg Pro His Ala Arg Lys Arg Val Ala Ala Lys Val Ser Tyr
                 5                  10                 15
Lys Glu Glu Ser Glu Ser Asp Gly Ala Gly Ser Gly Ser Asp Phe Glu Pro
                20                  25                 30
Ser Ser Gly Glu Gly Gln His Ser Ser Asp Glu Asp Cys Glu Pro Gly Pro
 35              40                  45                 50
Cys Lys Gln Lys Arg Ala Ser Ala Pro Gln Arg Thr Lys Ala Gly Ser Lys
                55                  60              65
Ser Ala Ser Lys Thr Gln Arg Gly Ser Gln Cys Glu Pro Ser Ser Phe Pro
 70              75                  80                 85
Glu Ala Ser Ser Ser Ser Gly Cys Lys Arg Gly Lys Lys Val Ser Ser
                90                  95              100
Gly Ala Glu Glu Met Ala Asp Arg Lys Pro Ala Gly Val Asp Gln Trp Leu
               105                 110                115
Glu Val Tyr Cys Glu Pro Gln Ala Lys Trp Val Cys Val Asp Cys Val His
120                 125                 130                135
Gly Val Val Gly Gln Pro Val Ala Cys Tyr Lys Tyr Ala Thr Lys Pro Met
               140                 145              150
Thr Tyr Val Val Gly Ile Asp Ser Asp Gly Trp Val Arg Asp Val Thr Gln
155                 160                 165                170
Arg Tyr Asp Pro Ala Trp Met Thr Ala Thr Arg Lys Cys Arg Val Asp Ala
                    175                 180                185
Glu Trp Trp Ala Glu Thr Leu Arg Pro Tyr Arg Ser Leu Leu Thr Glu Arg
               190                 195                 200
Glu Lys Lys Glu Asp Gln Glu
205                 210
```

(2) INFORMATION FOR SEQ ID NO: 2:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO: 2:

```
Gln Arg Arg Pro His Gly Arg Glu Arg Arg Val Ala Ser Arg Val Ser Tyr
                 5                  10                 15
Lys Glu Glu Ser Gly Ser Asp Gly Ala Gly Ser Gly Ser Asp Phe Glu Leu
                20                  25                 30
Ser Ser Gly Glu Ala Ser Asp Pro Ser Asp Glu Asp Ser Glu Pro Gly Pro
 35              40                  45                 50
Pro Lys Gln Arg Lys Ala Pro Ala Pro Gln Arg Thr Lys Ala Gly Ser Lys
                55                  60              65
Ser Ala Ser Arg Thr His Arg Gly Ser His Arg Lys Asp Pro Ser Leu Pro
 70              75                  80                 85
Ala Ala Ser Ser Ser Ser Ser Ser Lys Arg Gly Lys Lys Met Cys Ser
                90                  95              100
Asp Gly Glu Lys Ala Glu Lys Arg Ser Ile Ala Gly Ile Asp Gln Trp Leu
               105                 110                115
Glu Val Phe Cys Glu Gln Glu Glu Lys Trp Val Cys Val Asp Cys Val His
120                 125                 130                135
```

Gly Val Val Gly Gln Pro Leu Thr Cys Tyr Lys Tyr Ala Thr Lys Pro Met
                140                 145                 150

Thr Tyr Val Val Gly Ile Asp Ser Asp Gly Trp Val Arg Asp Val Thr Gln
        155                 160                 165                 170

Arg Tyr Asp Pro Val Trp Met Thr Val Thr Arg Lys Cys Arg Val Asp Ala
                175                 180                 185

Glu Trp Trp Ala Glu Thr Leu Arg Pro Tyr Gln Ser Pro Phe Met Asp Arg
        190                 195                 200

Glu Lys Lys Glu Asp Leu Glu
205                 210

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (xi) SEQUENCE DESCRIPTION: SEQ ID NO: 3:

GAAGAGAGGG GGTACCATGA ATGAAG                          26

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO: 4:

GAGGAGCCTC CTGGATCCGC AGTC                            24

(2) INFORMATION FOR SEQ ID NO: 5:

(i) SEQUENCE CHARACTERISTICS:
        (A) LENGTH: 1679 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 5:

GCTGCAGTGA TCCAGGGGAC CCCACAAATG GTGCAGCAAA AAAGAAAGTG          50

GCCAAAGCCA CTGCTAAATC CAAGAATCTC AAGGTTCTGA AGGAGGAAGC        100

ACTCAGCGAC GGGGATGACT TCCGGGACTC ACCAGCTGAC TGCAAGAAGG        150

CAAAGAAACA CCCAAAAAGC AAGGTGGTGG ACCAAGGCAC TGATGAAGAT        200

GACAGTGAGG ATGACTGGGA GGAGGTGGAA GAGCTTACTG AACCTGTGCT        250

GGACATGGGA GAAAATTCTG CCACCTCACC GTCTGACATG CCTGTGAAGG        300

CGGTGGAGAT TGAGATTGAA ACACCACAGC AGGCGAANNN ANGNGAAAGA        350

AGTGANAAGA TANANNTGGA GTTTGAGACA TANCTCCGGA GGNNGATGAA        400

| | |
|---|---|
| NCGTTTCAAT AAAGGGGTCC ATGAGGACAC ACACAAGGTT CACCTTCTCT | 450 |
| GCCTGCTAGC AAATGGCTTC TATCGAAATA ACATCTGCAG CCAGCTCGAT | 500 |
| CTGCTGGCCA TTGGCCTCTC CATCATCCCA ATTCGCTTTA CCAAGGTGCC | 550 |
| ACTTCAAGAT AGGGATGCCT ACTACCTTTC AAACCTGGTA AAGTGGTTCA | 600 |
| TCGGAACCTT CACTGTCAAC GCTGACCTTT CAGCCAGCGA GCAGGACGAC | 650 |
| CTGCAGACCA CCTTGGAAAG GAGGATTGCC ATTTACTCTG CGAGGGATAA | 700 |
| TGAAGAGTTG GTCCATATAT TTCTTCTGAT TCTTCGGGCT CTGCAGCTGC | 750 |
| TCACCCGGCT GGTCTTGTCT CTGCAGCCCA TTCCACTGAA GTCAGCTGTG | 800 |
| ACAAAGGGGA GGAAATCTTC CAAGGAGACA TCTGTAGAGG GTCCTGGAGG | 850 |
| TTCTTCAGAA CTCTCTAGTA ACAGTCCAGA AAGCCACAAC AAACCTACGA | 900 |
| CCAGCAGGAG AATCAAAGAA GAAGAAACCT TGTCTGAGGG CAGAGCCAAA | 950 |
| CCAACCGCCA GGGGAAGAG AGGCACAGGC ACTGCGGGCA GCAGGCAGCG | 1000 |
| GAGGAAGCCC TCTTGCAGCG AGGGAGAGGA GGCCGAGCAG AAAGTCCAGG | 1050 |
| GCCGTCCACA TGCCCGGAAG CGGCGTGTGG CTGCCAAGGT GTCATACAAA | 1100 |
| GAGGAGAGTG AGAGCGATGG GGCAGGCAGC GGCTCTGACT TTGAACCGTC | 1150 |
| CAGTGGGGAG GGCCAGCATT CCTCTGATGA GGATTGTGAG CCTGGCCCTT | 1200 |
| GCAAGCAGAA GAGGGCCTCA GCTCCTCAGA GGACAAAGGC TGGGTCTAAG | 1250 |
| AGTGCTTCCA AGACCCAACG CGGAAGCCAG TGTGAGCCGT CAAGCTTTCC | 1300 |
| GGAGGCGTCT TCAAGCTCTT CAGGCTGTAA GAGAGGCAAG AAGGTTTCCA | 1350 |
| GTGGTGCTGA AGAGATGGCA GATAGGAAAC CTGCTGGTGT AGACCAGTGG | 1400 |
| CTGGAGGTGT ACTGTGAGCC ACAGGCAAAG TGGGTGTGTG TGGACTGTGT | 1450 |
| ACATGGTGTG GTGGGCCAGC CTGTGGCCTG TTACAAATAT GCCACCAAAC | 1500 |
| CCATGACCTA TGTTGTAGGC ATTGACAGTG ATGGCTGGGT CCGAGATGTT | 1550 |
| ACTCAGAGGT ATGACCCAGC CTGGATGACC GCAACCCGCA AGTGCCGGGT | 1600 |
| TGATGCTGAG TGGTGGGCTG AGACCTTGAG ACCCTATCGG AGCCTACTTA | 1650 |
| CGGAGAGGGA GAAGAAGGAA GACCAGGAG | 1679 |

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO: 6:

| | |
|---|---|
| GCTGCAGTGA TCCAGGGGAC | 20 |

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic -continued (iii) HYPOTHETICAL: NO (xi) SEQUENCE DESCRIPTION: SEQ ID NO: 7:

TGGACGGTTC AAAGTCAGAG                                               20

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO: 8:

AGCTGCAGCT GGATCGCAGC GCTGCCTTTC C                                  31

(2) INFORMATION FOR SEQ ID NO: 9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO: 9:

TCGAGCTCTG TTGATACGTC CACAATTACA CCTC                               34